United States Patent
Mullis et al.

(10) Patent No.: US 6,261,255 B1
(45) Date of Patent: Jul. 17, 2001

(54) APPARATUS FOR VASCULAR ACCESS FOR CHRONIC HEMODIALYSIS

(76) Inventors: Ronald Jay Mullis, 2088 Winchester Pl., Fayetteville, AR (US) 72701; William R. McNair, 3302 N. North Hills Blvd., Fayetteville, AR (US) 72703

( * ) Notice: Subject to any disclaimer, the term of this patent is extended or adjusted under 35 U.S.C. 154(b) by 0 days.

(21) Appl. No.: 09/188,034

(22) Filed: Nov. 6, 1998

(51) Int. Cl.$^7$ .............................. A61M 5/00; A61M 39/00
(52) U.S. Cl. ............................ 604/8; 604/6.16; 604/175; 606/158
(58) Field of Search .................. 604/8, 6.16, 164.06, 604/164.07, 175; 606/158

(56) References Cited

U.S. PATENT DOCUMENTS

| | | | |
|---|---|---|---|
| 3,434,869 | 3/1969 | Davidson | 117/94 |
| 3,633,585 | 1/1972 | McDonald, Jr. | 128/348 |
| 3,713,441 | * 1/1973 | Thomas . | |
| 3,818,511 | * 6/1974 | Goldberg et al. . | |
| 3,953,566 | 4/1976 | Gore | 264/288 |
| 4,133,312 | * 1/1979 | Burd . | |
| 4,160,454 | 7/1979 | Foux | 128/348 |
| 4,187,390 | 2/1980 | Gore | 174/102 |
| 4,239,042 | 12/1980 | Asai | 128/214.4 |
| 4,816,339 | 3/1989 | Tu et al. | 428/421 |
| 4,834,721 | 5/1989 | Onohara et al. | 604/266 |
| 4,842,582 | * 6/1989 | Mahurkar . | |
| 4,898,591 | 2/1990 | Jang et al. | 604/282 |
| 5,061,276 | 10/1991 | Tu et al. | 623/1 |
| 5,090,954 | 2/1992 | Geary | 604/29 |
| 5,116,360 | 5/1992 | Pinchuk et al. | 623/1 |
| 5,163,951 | 11/1992 | Pinchuk et al. | 623/1 |
| 5,360,397 | 11/1994 | Pinchuk | 604/27 |
| 5,529,820 | 6/1996 | Naomi et al. | 428/364 |
| 5,702,372 | 12/1997 | Nelson | 604/264 |
| 5,709,672 | 1/1998 | Illner | 604/265 |
| 5,749,880 | 5/1998 | Banas et al. | 606/198 |
| 5,755,775 | 5/1998 | Trerotola et al. | 623/1 |
| 5,759,173 | 6/1998 | Priessman elt al. | 604/96 |
| 5,769,830 | 6/1998 | Parker | 604/282 |
| 5,788,626 | 8/1998 | Thompson | 600/36 |

\* cited by examiner

*Primary Examiner*—Corrine McDermott
*Assistant Examiner*—Choon P. Koh
(74) *Attorney, Agent, or Firm*—Head, Johnson & Kachigian

(57) ABSTRACT

The invention includes a composite tube for forming an arteriovenous fistula with at least two conjoined segments or sections. The first section includes an elongated tubing formed from PTFE or another catheter material that is similarly amenable for convenient arterioveneous access. The second section includes an elongated tubing formed from silicone or another suitable long term catheter material. An intermediate connection couples the first section to the second section. The diameter of the first segment is between 2 mm. to 10 mm. while the second segment is between 4 to 8 millimeters at the coupling site and tapers to approximately 3 to 4 mm. distally. The second segment includes outlet ports proximate a beveled tip permitting outward blood flow. Several intermediate connections may be employed including single composite tubing, flanged segments and male and female tabbed collars, as long as the connection allows uninterrupted laminar flow across the entire length of the arteriovenous fistula. A method of inserting the apparatus into the venous system wherein the second section will have a freely moving venous end that resists occlusion and/or clogging as well.

14 Claims, 4 Drawing Sheets

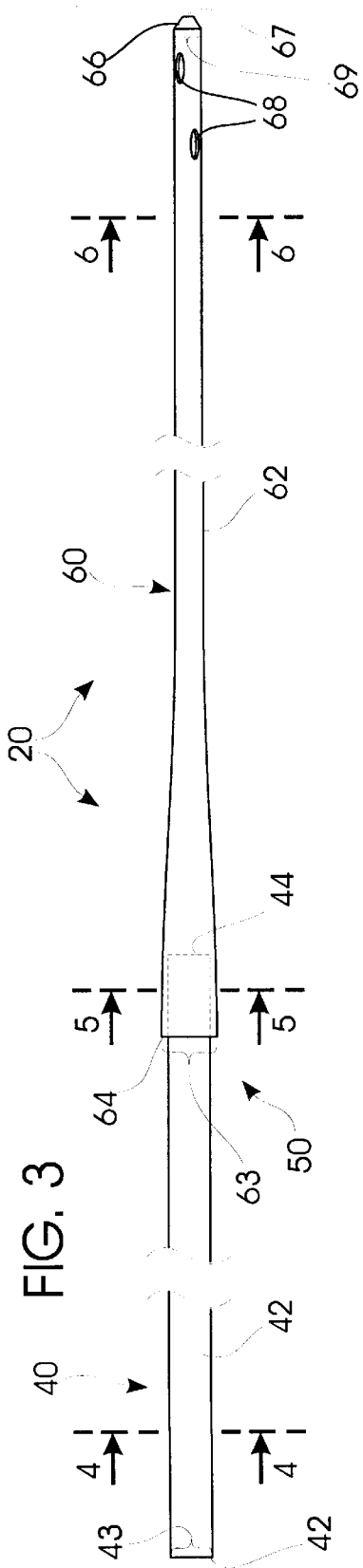
FIG. 3
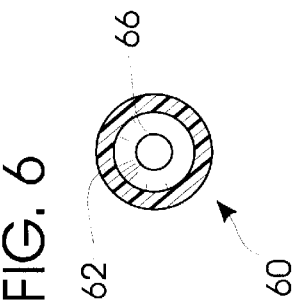
FIG. 6
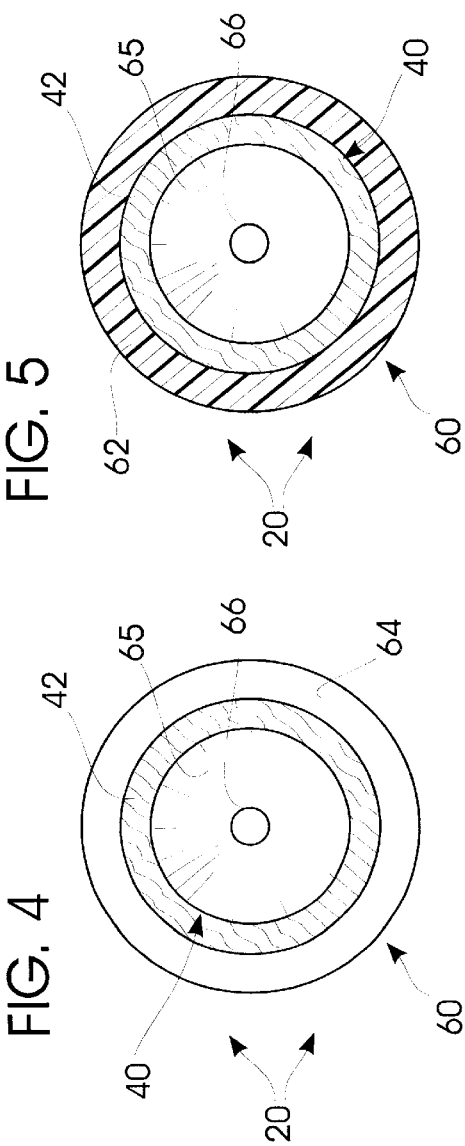
FIG. 5
FIG. 4

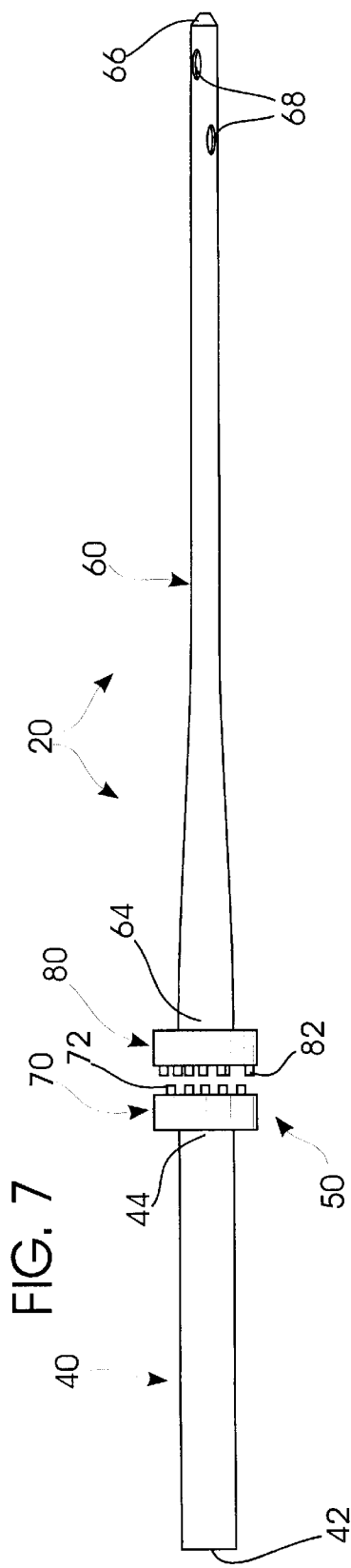
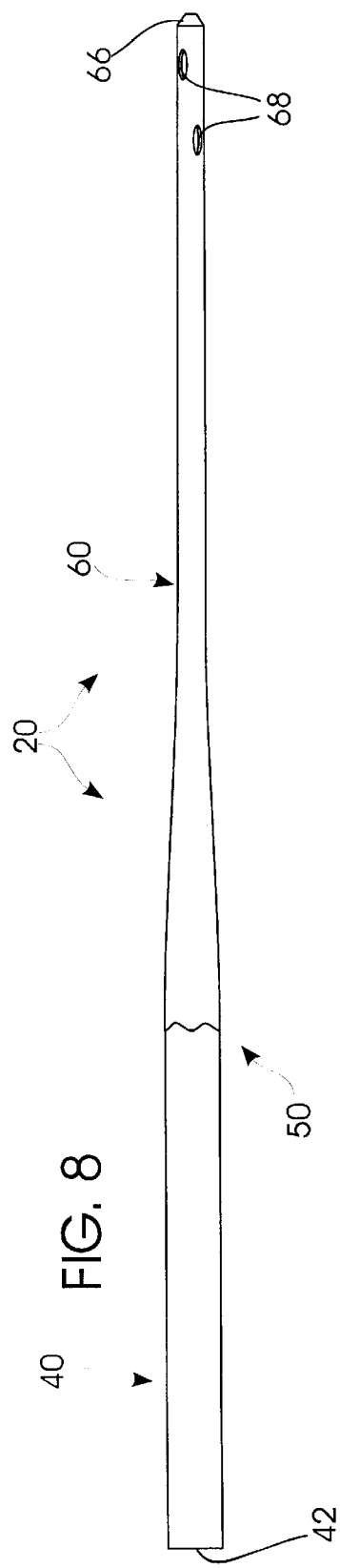

APPARATUS FOR VASCULAR ACCESS FOR CHRONIC HEMODIALYSIS

BACKGROUND OF THE INVENTION

1. Field of the Invention

The invention relates generally to an apparatus that facilitates vascular access for patients. In particular, the invention relates to an extended use tubing apparatus that is inserted into a patient to facilitate vascular access for chronic hemodialysis treatment. The tubing provides an arteriovenous fistula that resists occlusion and/or clogging.

2. Known Art

Over 130,000 patients undergo chronic hemodialysis in the United States each year as treatment for renal failure. Conventional hemodialysis treatment requires extensive and often extended, long-term vascular access. Access to the blood supply is generally sought through the vasculature, which is usually accomplished by establishing a native artery to vein arteriovenous fistula or by placement of a prosthetic graft fistula.

The Brescia-Cimino direct radio-cephalic fistula is a preferred form of permanent access to the vasculature. In this surgery, and in other native arteriovenous fistulas a communication is established between an artery traversing a limb (i.e. the arm or leg) and a corresponding vein in the same limb. If acceptable vasculature is not available then a prosthetic graft is employed to create a fistula for vascular access. Unfortunately, all types of vascular access are known to have a high failure rates and associated high costs of treatment. Vascular access often eventually fail due to the formation of scar tissue inside the vessel or due to vessel occlusion. Other common causes of graft failure are technique errors, infection, and neointimal hyperplasia at the distal anastomosis (venous) and within polytetraflouroethylene (PTFE) graft segments. Hyperplasia or buildup of fibrin at the venous anastomosis is probably the leading threat to most A-V fistulas. Arterial occlusive problems are less commonly the primary cause of fistula failure. As will be readily appreciated by those skilled in the art, failure of hemodialysis access contributes to morbidity, hospitalization time, and the cost of treatment.

While percutaneous interventional techniques (such as angoiplasty, atherectomy, and stent placement) are becoming increasingly popular in the management of hemodialysis access graft complications, these techniques are also generally prone to failure for the same reasons as the original fistula, necessitating further surgical revision. Such revision usually consists of the implanting of a PTFE interposition graft, and offer 30-day patencies of about 44–65%.

PTFE interposition grafts are also often placed in patients who have failed native fistula. Usually, these fistulae retain a small segment of patent vein beyond the anastomosis, and have reconstitution of veins further up the arm via collaterals. An interposition prosthetic graft is used to bridge the artery and vein.

Various types of highly flexible, non-porous tubings have been previously proposed for various medical applications. These applications typically involve the insertion of the tubing into a living body, either temporarily or as a permanent implant. Temporary applications include the use of the tubing as a catheter tubing to convey fluids into or out of a body, or alternatively as the tubing portion of a medical device such as an endoscope. For example, present endoscope channel tubes are made of porous expanded PTFE having a microstructure of nodes interconnected by fibrils, made as taught by U.S. Pat. Nos. 4,187,390 and 3,953,566.

These tubes typically have a very small pore size with a fibril length of less than five microns. They are quite flexible, inert, biocompatible and lubricious. However, due to the porosity of the tubing, during use various contaminants such as proteins and calcium tend to penetrate the void spaces present on the inner surface of the tube and to adhere to the inner surface. The adhesion of contaminants to the inner surface of the tube result in a decline in the slip properties of the inner surface, and also impaired other tube functions such as its flexing properties. Moreover, washing and sterilization were necessary in order to remove the contaminants so that the tube could be reused and such washing and sterilization were time consuming, and represented a burdensome operation.

Thus, there exists a need in the art for an improved apparatus for establishing reliable, long-term access to a patient's vasculature for chronic hemodialysis treatment. In particular, there exists a need for a fistula that facilitates subsequent remedial revisions including the removal and/or replacement of portions of the tubing. An ideal tubing should promote uninhibited blood flow through the tubing while resisting clogging or other occlusions.

SUMMARY OF THE INVENTION

The present invention addresses the problems associated with the known art. The invention includes a composite tubing graft with at least two conjoined sections. The first section includes an elongated tubing formed from PTFE, silicone, fluorosilicone or another catheter material that is similarly amenable for convenient arteriovenous access. The second section includes an elongated tubing formed from silicone or another suitable long-term catheter material. An intermediate connection couples the first section to the second section.

The first segment (i.e. the PTFE segment) is commercially available in varying lengths or rolls. The preferred diameters for the first segment are from between two millimeters to ten millimeters. The second segment (i.e. the silicone segment) is also commercially available in varying lengths. Ideally, the segment has a diameter of four to eight millimeters at the coupling site and tapers to approximately three to four millimeters distally. In an exemplary embodiment, the segment includes a radio-opaque strip proximate the terminus. While various connectors are suitable for use with the invention (including conventional luer fittings and the like), the selected connector must not inhibit blood flow, must be entirely extraluminal, and must provide for subsequent interchangeability of the first and second segments.

A method of inserting the apparatus into the venous system without an anastomosis to reduce graft failures compared to current methods also enables the tubing graft to be advantageously deployed in many patients. A significant advantage of the insertion method for the tubing graft is that the surgeon may avoid anchoring the second section in the venous system without a venous anastomosis. Consequently, the second section will have a freely moving venous end that resists clogging. (In percutaneously placed temporary venous catheters, it has been suggested that it is the free mobility of the catheter tip which is important in preventing and/or reducing clogging.)

The method for inserting the graft is as follows. Anatomic sites are selected and evaluated. Then, surgical antisepsis is achieved. The appropriate length and diameter composite graft is chosen according to the size of the selected artery and vein and distances therebetween. The distal end of the PTFE segment is sutured to a functioning artery using standard vascular techniques including systemic heparinization. Arterial inflow is assured. The appropriate vein is located and controlled with vascular tapes. The PTFE segment is tunneled subcutaneously close to the level of the vein. A venotomy is made and the silicone segment of the graft is inserted into the vein. An intraluminal trocar can assist with this insertion. The trocar is removed and venous back bleeding noted. In an alternate technique, the silicone segment (venous limb) can be inserted into a more proximal or central vein with standard peel-away technique. After insertion into the central vein, the distal silicone segment is tunneled subcutaneously to meet with the PTFE segment. The two segments are conjoined and flow established across the fistula. Adequate flow is determined with palpation for thrill and auscultation for bruit.

The invention also addresses problems related to PTFE intimal buildup by providing for subsequent graft cleaning that does not necessitate having to suture the graft. The invention also enables subsequent revision of the venous access under local anesthesia without requiring significant, often life-threatening, surgery. This avoids painful and expensive procedures for maintaining long term vascular access.

Since PTFE graft failures often mandate prompt revision, another important contribution of the present invention is the reduction of such failures. Since failure usually results from fibrin buildup at the distal venous anastomosis, one manner in which the invention reduces failures is by circumventing the necessity of a venous anastomosis.

Moreover, revision of this composite graft can easily be accomplished under only local anesthesia and employing standard vascular surgery principles including systematic heparinization. The steps for revision include the following. Location and control of the conjoined segment of the graft is obtained. The conjoined attachment is released. The PTFE segment is opened and cleaned with standard embolectomy techniques. The silicone segment can be removed over a guide wire which is inserted into the vein. A new silicone segment is selected (the replacement silicone segment should be three to four centimeters longer to assure that the catheter tip lies proximal to any fibrin deposits that may have accumulated in the vein) and implanted in the patient. After blood flow is assured, the new silicone segment and the PTFE segment are conjoined.

Thus, a principal object of the present invention is to provide an apparatus that permits reliable, long-term vascular access for chronic hemodialysis.

Another object of the present invention is to provide an improved composite tubing that may be advantageously inserted in a patient to form an arteriovenous fistula.

Yet another object of the present invention is to provide a multiple segment tubing wherein each segment maybe easily maintained.

A related object of the present invention is to provide tubing that may be replaced without necessitating major surgery and/or complete patient anesthesia.

A basic object of the present invention is to provide a more effective vascular access for chronic hemodialysis to prolong the life expectancy of a patient.

Another object of the present invention is to provide an improved method for inserting arteriovenous tubing obviating the need for venous anastomosis.

Another object of the present invention is to provide a venous tubing for an arteriovenous fistula that preserves the mobility of the venous catheter terminus.

Another object of the present invention is to allow thrombectomy of the existing graft without having to cut and suture the graft. This easily accomplished under local anesthesia.

Another object of the present invention is to allow relocation of a free-floating silicone segment under local anesthesia.

Another object of the present invention is to have a graft system that allows for laminar flow across the entire length of the graft, which prevents turbulence and fibrin deposition.

BRIEF DESCRIPTION OF THE DRAWINGS

FIG. 3 is a partially fragmented elevational view of an exemplary embodiment of the multiple component tubing;

FIG. 4 is a cross-sectioned view taken along lines 4—4 of FIG. 3;

FIG. 5 is a cross-sectioned of view taken along line 5—5 of FIG. 3;

FIG. 6 is a cross-sectional view taken along line 6—6 of FIG. 3;

FIG. 7 is a partially fragmented elevational view of an exemplary embodiment of the multiple component tubing; and, FIG. 8 is a partially fragmented elevational view of an exemplary embodiment of the multiple component tubing.

DETAILED DESCRIPTION OF THE PREFERRED EMBODIMENTS

Figure 1:
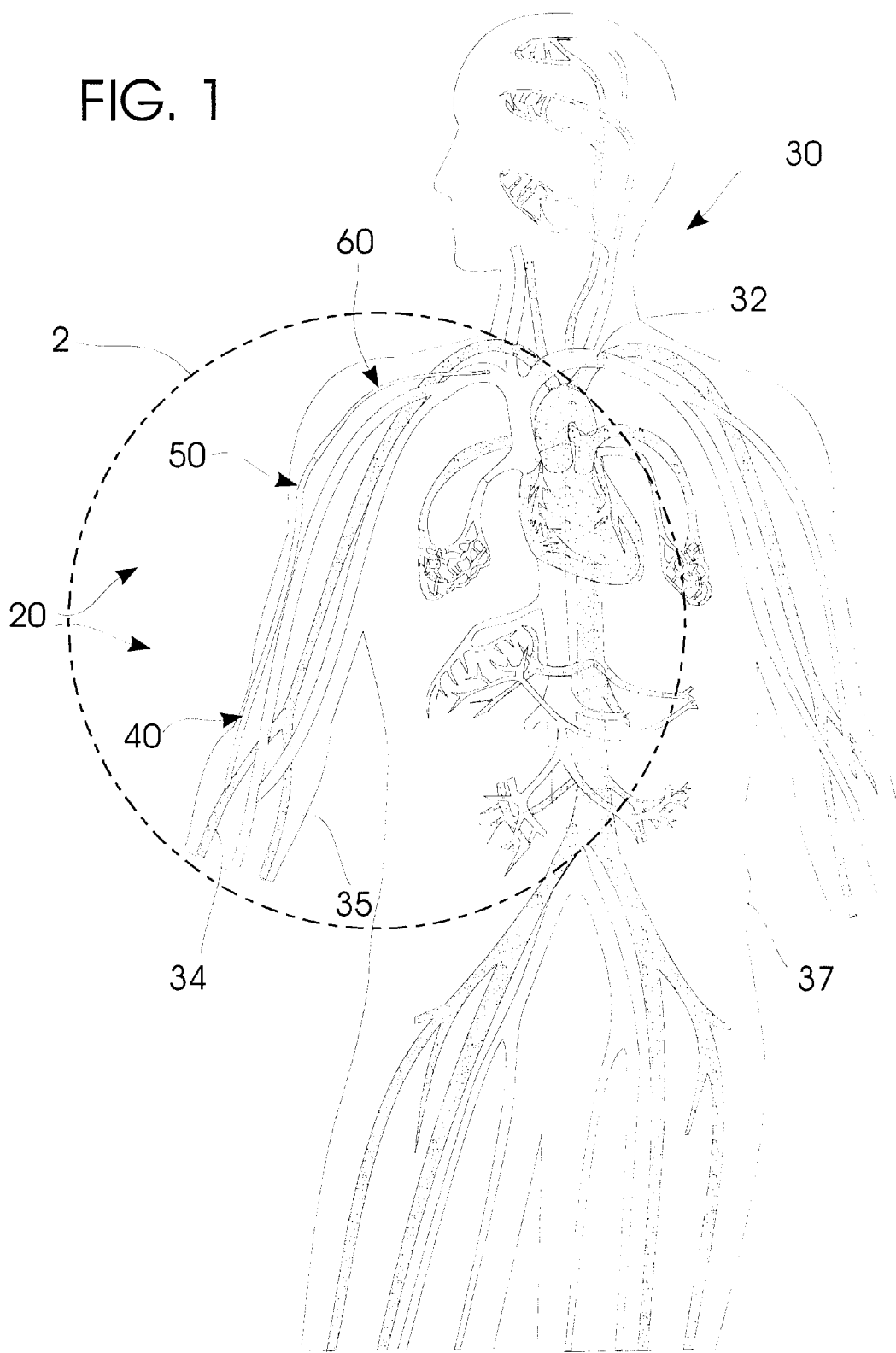
FIG. 1 is a schematic diagram of the human body with the improved multiple segment tubing employed to establish an arteriovenous fistula.
Figure 2:
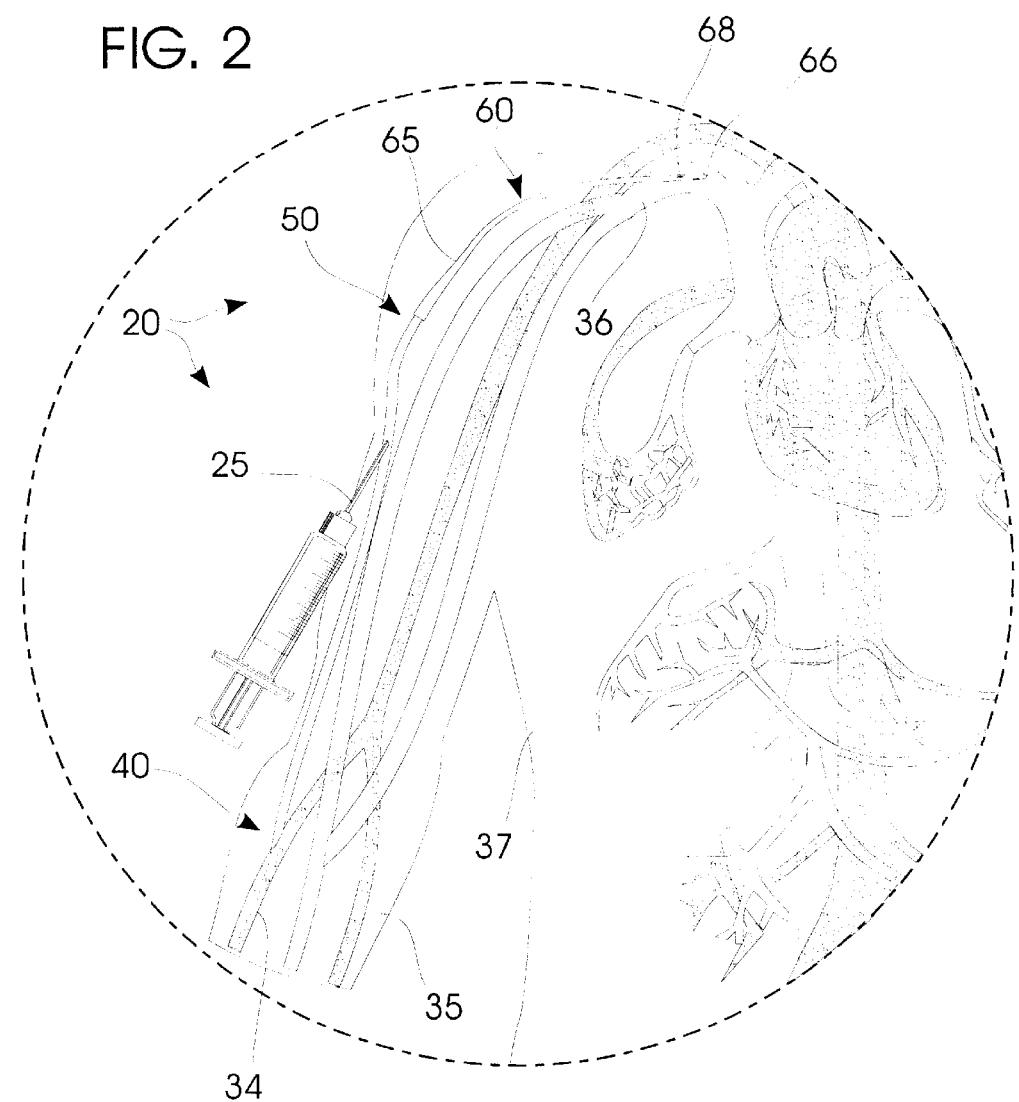
FIG. 2 is an enlarged schematic view of the encircled portion of FIG. 1.

The apparatus for vascular access for hemodialysis is generally designated by referenced numeral 20 and FIGS. 1–6. The apparatus 20 may also be referred to as a multiple component tubing, composite graft or the like. The multiple component tubing 20 may be advantageously deployed to form an arteriovenous fistula in a patient 30. In such a deployment, the tubing is inserted into the patient subcutaneously to form a bridge between an artery and a vein in the patient's vasculature 32.

The tubing 20 preferably comprises an elongated flexible conduit with multiple sections or segments that are coupled together. In an exemplary embodiment, the first segment 40 is adapted to be connected to an artery 34 in limb 35. Of course, other arteries and other limbs may be chosen as well. The first segment 40 couples through an intermediate section 50 to a second segment 60. The second section 60 connects to a vein 36 in the patient's trunk 37. Of course, other veins in trunk 37 may alternatively be chosen.

The first section 40 comprises an elongated flexible tube 42 extending between spaced apart ends 44 and 46. The tube 42 defines an internal conduit shaft 48 that conducts entering blood therethrough. Ideally, tube 42 is formed from PTFE. However, tube 42 can be formed from any other acceptable material that may be easily penetrated by a needle 25. Such needles are commonly employed when conducting hemodialysis. PTFE is particularly suitable because it is easily penetrated and it has a propensity for self-sealing.

Tube 42 may be cut from a continuous roll of such material. As mentioned previously, tube 42 defines distinct, spaced apart ends 44 and 46. Ideally, end 46 is inserted into the artery or connected to the artery in an abutting suture commonly practiced in the art. Tube 42 has a diameter that is constant throughout its length, preferably between 2 and 10 mm. Ideally, the diameter is between 4 and 6 mm. Of course, since each patient varies in the length of their limb 35, the length of tubing 42 will vary as well. Ideally, the tube 42 will extend from its juncture with the artery subcutaneously along the limb until a point proximate the juncture of limb 35 with the trunk 37.

The intermediate section 50 establishes a juncture between the first section 40 and second section 60. Juncture 50 may be formed by a simple overlap of the first and second sections 40 and 60, or it may be a separate fitting such as a conventional luer fitting or the like. (FIGS. 3, 7–9). The primary concern is that the juncture 50 form a stable, sealed connection between the two tubes 42 and 62. This may be accomplished by tightly fitting the tubes together or by permanently affixing the two tubes. Methods for permanently affixing the two tubes include sonic welding, adhering (i.e. by gluing or the like) or any other similar conventional technique for adjoining such components. The primary concern is that the connection 50 permit either tubing segment 40 or 60 to be subsequently replaced as necessary. Another important consideration is that the juncture 50 promote unrestricted fluid flow therethrough. In particular, it is important to maintain luminar flow through tubing 20.

Tubing section 60 comprises an elongated hollow tube 62 with spaced apart ends 64 and 66 that preferably tapers from end 64 to end 66. The terminal end 66 includes a pair of outlet ports 68. The outlet ports 68 enable the blood flowing through the tubing 20 to be emitted therefrom to promote continuous and unhindered fluid flow. The end 64 connects to the first section 40 at the juncture 50. The tube 62 includes a intermediate tapered section 65 extending adjacent end 64. The tapered section 65 begins with an interior diameter (between 2 and 10 mm.) that corresponds to the diameter of first segment end 44. Thus, the ends may be made as is shown in FIG. 3. The diameter of tapered section 65 then decreases to a smaller diameter (generally approximately 3 to 4 mm). The end 66 forms a beveled tip with spout 67 for the emission of blood flowing through the tubing 20. End 66 comprises a reduced diameter 69 that encourages blood flow through ports 68.

Ideally, the venous catheter 60 is not secured to the vein using a conventional venous anastomosis. Rather, the catheter tip 66 extends for a length inside the vein and the catheter portion 69 abutting the vein is secured adjacent the catheter inlet into the vein. Thus, the catheter end portion 66 can "float" inside the vein to prevent occlusions.

The tubing assembly 20 can be inserted into a patient during a normal anesthetized procedure while subsequent revisions can be accomplished using only local anesthetic and conventional balloon techniques. The arterial catheter is attached using known arterial securing techniques. Preferably, the arterial connection is made in an artery 34 in limb 35. Limb 35 may be either arm or either leg. Also, the preferred venous connection is established upstream of the limb 35 connections to the trunk 37. It is especially preferred to establish the venous connection upstream of the vein intersections for each limb 35. These veins are approximately 3–20 mm. in diameter and they establish a ratio of vein diameter to tubing diameter 63 is at least 2:1.

In another exemplary embodiment, a collar coupling 70 and 80 is formed at each end 44 and 64 of each tube segment 40 and 60 (FIG. 7). These collars 70, 80 may be coupled together by squeezing them together, coapting with a leurlok and subsequently applying glue or heat or sonic welding or the like. This coupling 50 establishes a suitable connection between the first and second segments 40 and 60. Ideally, each collar 70 and 80 has both male tabs 72 and 82 and corresponding female receivers (not shown).

During insertion, the surgeon selects the appropriate lengths of the tubing segments 40 and 60. Then, they are coupled by simply pressing the collars together to set the tabs in the recesses. Thus, the connection 50 is formed. The tubing segments 40 and 60 may be supplied in various lengths with the collars 70 and 80 forming the terminal portion adjacent each end 44 and 66 respectively. Alternatively, the collars may be supplied as separate components with a smaller diameter flange upon which the respective ends 44 and 66 are placed. Subsequent sealing will affix the respective ends to the flange and permit the collars use in a more permanent manner.

In yet another exemplary embodiment, the tubing 20 may comprise a composite bonded multiple component tube wherein the tubes are joined at connection 50 (FIG. 8). In this particular embodiment, the ends 46 and 66 are trimmed or otherwise adjusted by the surgeon prior to the tubing insertion. Thus, the ends 46 and 66 are selectively defined depending upon the insertion parameters for a particular patient when the connection 50 is integrally formed and constant.

In another exemplary embodiment, a conventional luer fitting 90 is employed to couple the first segment 42 to the second segment 60 (FIG. 9). The coupling may use ribbed 92 and 94 flanges to seat the respective ends 44 and 64 of the segments. They may be selectively adhered, welded, or otherwise secured as necessary as well.

In some patients, it may be desirable to further secure the coupling with appropriate sutures or the like adjacent the coupling 50 and subcutaneously to prevent undesirable migration of either the arterial or venous segment 40 or 60.

Regardless of the type of connection 50 established, the overriding concern is that the coupling 50 establish a semi-permanent juncture between the first and second segments 40 and 60 that prevents leakage while maintaining fluid flow between the respective segments 40 and 60. Moreover, there should be no more impendence to flow. Another consideration is the coupling easily facilitates subsequent revision of either segment 40 or 60 to enable the removal and or replacement of the respective segment 40 or 60 as necessary. Thus, the surgeon may, under only local anesthetic, selectively replace either segment 40 or 60 as necessary in the result of a partial occlusion clogging, or undesirable scarring, or other fluid flow hindering development.

A method of inserting the apparatus into the venous system without an anastomosis to reduce graft failures compared to current methods also enables the tubing graft to be advantageously deployed in many patients. A significant advantage of the insertion method for the tubing graft is that the surgeon may avoid anchoring the second section in the venous system with a venous anastomosis. Consequently, the second section 60 will have a freely moving venous end 66 that resists clogging. (In percutaneously placed temporary venous catheters, it has been suggested that it is the free mobility of the catheter tip which is important in preventing and/or reducing clogging.)

The method for inserting the graft is as follows. Anatomic sites are selected and evaluated until a suitable candidate is located (i.e. when the first, PTFE, and second sections, silicone, are to be placed in a central artery/vein, radiographic location is done). Then, surgical antisepsis is achieved. The appropriate length and diameter composite graft is chosen according to the size of the selected artery and vein and distances therebetween. The distal end of the PTFE segment is sutured to a functioning artery using standard vascular techniques including systemic heparinization. Arterial inflow is assured. The appropriate vein is located and controlled with vascular tapes. The PTFE segment is tunneled subcutaneously near to the level of the vein. A venotomy is made and the silicone segment of the graft is inserted into the vein. An intraluminal trocar can assist with this insertion. The trocar is removed and venous back bleeding noted. In a preferred technique, the silicone segment (venous limb) can be inserted into a more proximal or central vein with standard peel-away technique. After insertion into the central vein, the distal silicone segment is tunneled subcutaneously to meet with the PTFE segment. The two segments are conjoined and flow established across the fistula. Adequate flow is determined with palpation for thrill and auscultation for bruit.

Whereas, the present invention has been described in relation to the drawings attached hereto, it should be understood that other and further modifications, apart from those shown or suggested herein, may be made within the spirit and scope of this invention.

What is claimed is:

1. An apparatus for providing vascular access for chronic hemodialysis, said apparatus adapted to be disposed interminally in a patient to form an arteriovenous fistula, said apparatus comprising:

a first segment adapted to connect with an artery in the patient, and wherein said first segment is comprised of a material chosen from the group suitable for repeated needle penetration to provide vascular access, said material selected from the group consisting of PTFE, silicone and fluorosilicone;

second segment adapted to be inserted into a vein in the patient and secured therein, said second segment having a tapered length culminating in a beveled tip and wherein said second segment is comprised of a catheter material suitable to resist clogging during subsequent use through the deployment of said tip in an unanchored state, said material selected from the group consisting of silicone, fluorosilicone and rubber;

an intermediate connecting portion coupling said first segment to said second segment; and, outlet ports proximate said tip for emitting fluids from said apparatus.

2. The apparatus as defined in claim 1 wherein said first segment defines a diameter and a length and wherein said diameter is constant across said length and wherein said second segment defines spaced apart ends and wherein one of said ends comprises a diameter equal to or larger than the diameter of said first segment and said other end comprises a smaller diameter.

3. The apparatus as defined in claim 2 wherein the ratio of the diameter of said vein to the diameter of said tip is 8 to 1.

4. The apparatus as defined in claim 1 wherein said intermediate connection is formed by said second segment overlapping a portion of said first segment.

5. The apparatus as defined in claim 1 wherein said intermediate connecting portion comprises a collar formed at the abutting ends of said first and second segments, said collar defining interlocking male tabs and female recesses.

6. The apparatus as defined in claim 1 wherein said intermediate connecting portion comprises an integral section wherein said first and second segment are joined by either sonic welding, adhesion, or the like.

7. A medical tubing for forming an internal arteriovenous fistula in a patient to provide vascular access for subsequent medical treatments, sad tubing comprising:

a first tube portion in fluid flow contact with an artery in a limb of the patient, said first portion anchored to said artery with a suture;

a second tube portion inserted into a vein in the patient, said second portion having a beveled tip defined in one end and outlet ports approximate said tip for emitting fluids from said tube, said ports adapted to be disposed inside the vein and said tube adapted to be free-floating in said vein and secured to said vein with a butterfly suture;

an intermediate portion coupling said first and second portions; and, whereby said first tube portion may be operatively coupled to said second tube portion by said intermediate portion to form a composite internal arteriovenous fistula.

8. The tubing as defined in claim 7 wherein said first portion is comprised of material adapted to permit needle puncture during said medical treatments, said material selected from the group consisting of PTFE, silicone, and fluorosilicone.

9. The tubing as defined in claim 8 wherein said second portion is chosen from the group consisting of silicone, flourosilicone, and rubber.

10. The apparatus as defined in claim 7 wherein said first portion defines a diameter and a length and wherein said diameter is constant across said length and wherein said second portion defines spaced apart ends and wherein one of said ends comprises a diameter equal to or larger than the diameter of said first portion and said other end comprises a smaller diameter.

11. The apparatus as defined in claim 10 wherein the ratio of the diameter of said vein to the diameter of said tip is 8 to 1.

12. The apparatus as defined in claim 7 wherein said tubing comprises an intermediate connection that is formed by said second portion overlapping an end of said first portion.

13. The apparatus as defined in claim 7 wherein said intermediate connection comprises an integral union wherein said first and second segment are joined by sonic welding, adhesion, heat fusion, or the like.

14. The apparatus as defined in claim 7 wherein said intermediate connection comprises a collar with male tabs and corresponding female receivers on mating ends of said first and second portions.

* * * * *